(12) United States Patent
Schuessler et al.

(10) Patent No.: US 11,078,085 B2
(45) Date of Patent: Aug. 3, 2021

(54) PRODUCTION OF ROUNDED SALT PARTICLES

(71) Applicant: Allergan, Inc., Irvine, CA (US)

(72) Inventors: David J. Schuessler, Santa Ana, CA (US); Alberto J. Flores-Pujol, Heredia (CR)

(73) Assignee: Allergan, Inc., Irvine, CA (US)

( * ) Notice: Subject to any disclaimer, the term of this patent is extended or adjusted under 35 U.S.C. 154(b) by 224 days.

(21) Appl. No.: 16/155,683

(22) Filed: Oct. 9, 2018

(65) Prior Publication Data

US 2019/0039911 A1    Feb. 7, 2019

Related U.S. Application Data

(63) Continuation of application No. 15/607,338, filed on May 26, 2017, now Pat. No. 10,093,548.

(Continued)

(51) Int. Cl.
*C01D 3/24* (2006.01)
*C01D 3/04* (2006.01)
(Continued)

(52) U.S. Cl.
CPC .............. *C01D 3/24* (2013.01); *C01D 3/04* (2013.01); *C01F 11/185* (2013.01); *C30B 31/02* (2013.01);
(Continued)

(58) Field of Classification Search
CPC . C01D 3/24; C01D 3/04; C01F 11/185; A61F 2002/0081; A61F 2/12; A61F 2240/001; C01P 2004/02; C01P 2004/60; C01P 2002/30; C01P 2004/32; C09C 3/041; C30B 31/02
See application file for complete search history.

(56) References Cited

U.S. PATENT DOCUMENTS 7,220,435 B2   5/2007  Dastidar et al.
8,313,527 B2  11/2012  Powell et al.
(Continued)

FOREIGN PATENT DOCUMENTS

CN   105693435   6/2016
EP     1545733   5/2007
(Continued)

OTHER PUBLICATIONS

Sharretts Plating Company, Inc., "A Guide to Vibratory Finishing Media—Types of Finishing Media", https://www.sharrettsplating.com/blog/a-guide-to-vibratory-finishing-media/, (Nov. 20, 2013). (Year: 2013).*
(Continued)

*Primary Examiner* — Michael N Orlando
*Assistant Examiner* — Christopher W Raimund
(74) *Attorney, Agent, or Firm* — Nathan S. Smith; Morgan, Lewis & Bockius LLP (57) ABSTRACT

The present disclosure generally relates to methods of preparing spherical salt particles for industrial, medical, and other uses. The methods can include combining the angular salt particles with a quantity of finishing media, for example, into a receptacle. Thereafter, the angular salt particles and the finishing media can be moved or agitated until the angular salt particles have a desired sphericity.

21 Claims, 9 Drawing Sheets

Related U.S. Application Data (60) Provisional application No. 62/342,011, filed on May 26, 2016.

(51) Int. Cl.
  *C01F 11/18* (2006.01)
  *C30B 31/02* (2006.01)
  *A61F 2/00* (2006.01)
  *A61F 2/12* (2006.01)

(52) U.S. Cl.
  CPC ......... *A61F 2/12* (2013.01); *A61F 2002/0081* (2013.01); *A61F 2240/001* (2013.01); *C01P 2002/30* (2013.01); *C01P 2004/02* (2013.01); *C01P 2004/32* (2013.01); *C01P 2004/60* (2013.01)

(56) References Cited

U.S. PATENT DOCUMENTS

| | | |
|---|---|---|
| 2004/0029699 A1 | 2/2004 | Lemaitre |
| 2005/0261399 A1 | 11/2005 | Hunkeler |
| 2007/0009589 A1 | 1/2007 | Raghupathi |
| 2009/0118829 A1 | 5/2009 | Powell et al. |
| 2009/0176096 A1 | 7/2009 | Mukhopadhyay et al. |
| 2009/0263475 A1 | 10/2009 | Manne et al. |
| 2011/0117267 A1 | 5/2011 | Powell |
| 2011/0278755 A1 | 11/2011 | Liu |

FOREIGN PATENT DOCUMENTS

| | | |
|---|---|---|
| EP | 2962757 | 1/2016 |
| GB | 1399001 | 6/1975 |
| GB | 2275876 | 9/1994 |
| JP | S 63-283564 | 11/1988 |
| JP | H 09-86923 | 3/1997 |
| NZ | 546777 | 9/2006 |
| WO | WO 00/29108 | 5/2000 |
| WO | WO 03/075881 | 9/2003 |
| WO | WO 03/082247 | 10/2003 |
| WO | WO 2009/048073 | 4/2009 |
| WO | WO 2010/003430 | 1/2010 |

OTHER PUBLICATIONS

Yokoyama et al., "Numerical Analysis of Movement of Balls in a Vibration Mill in Relation with Its Grinding Rate", KONA Powder and Particle Journal, No. 11 (1993). (Year: 1993).*

Chen et al., "Fluidized bed film coating of cohesive Geldart group C powders," Powder Technology, Feb. 2009, vol. 189, Issue 3, pp. 466-480.

Geology.com, "Tumbled Stones," 2005, retrieved from https://geology.com/rock-tumblers/tumbled-stones/, 8 pages.

International Search Report and Written Opinion from PCT/US2017/034842, dated Aug. 25, 2017, 9 pages.

International Search Report and Written Opinion from PCT/US2017/049490, dated Dec. 7, 2017, 11 pages.

* cited by examiner

PRODUCTION OF ROUNDED SALT PARTICLES

CROSS-REFERENCE TO RELATED APPLICATIONS

This application is a continuation of U.S. patent application Ser. No. 15/607,338, filed on May 26, 2017, which claims the benefit of and priority to U.S. Provisional Application No. 62/342,011, filed May 26, 2016, the entirety of each of which is incorporated herein by reference.

BACKGROUND

Field

The present disclosure generally relates to spherical salt particles, and more specifically relates to methods of making spherically shaped, or nearly spherically shaped, salt particles for industrial, medical, culinary, or other uses.

Background

Crystals develop their crystalline shape due to the manner in which growth occurs along different crystallographic planes. For example, common salt, or sodium chloride (NaCl), naturally forms as cubic crystals.

Many industrial and manufacturing processes use sodium chloride. For example, the textile, dairy, food, fertilizer, paper, and pharmaceutical industry all use sodium chloride to some degree. The flow properties of salt are important in many of these applications. Natural sodium chloride crystals do not have ideal flow characteristics. For example, salt particles, when used in a fluid state, have a tendency towards agglomerations. This is partially due to the angular nature of salt particles.

For many industrial and other applications, it would be beneficial to improve the flow properties of salt particles. Generally, particles that are rounded or spherical in shape tend to behave with more fluidity than otherwise identical particles that are angular in shape. If salt particles were readily available in rounded or spherical form, many of the industrial processes that rely on them might be benefited or improved because improved flow properties. Even consumers of salt for flavoring of food may benefit from salt that more predictably or smoothly flows from its container.

Additionally, in the medical device field, salt can be used to create texture on medical implants, for example, textured breast implants. In this application, salt particles are used as a sacrificial material that is applied to a sticky or fluid elastomeric material, such as silicone. After application of salt, the silicone is cured or allowed to set or solidify. The salt particles are then removed, thereby revealing a silicone material having a textured surface. For these and other applications, it can be appreciated that it would oftentimes be desirable that the sacrificial salt used is as uniform in size and shape as possible, for example, in order to create a predictable and uniform porosity leading to more optimal weight/strength ratio of the product. Rounded or spherical salt particles for use as a texturing material may help to form a texture that has a less angular topography than a texture made using angular salt particles. For example, as disclosed in U.S. Pat. No. 8,313,527, the entirety of which is incorporated herein by reference, elastomeric silicone materials that are textured using rounded salt particles have improved physical properties, such as improved strength, relative to otherwise identical elastomeric silicone materials that have been textured using angular salt particles.

Several methods have been developed and are reported to produce rounded or spherical salt in the particle size range of common table salt (e.g., about 100 μm to about 500 μm). These methods include, for example, evaporative processes that change the crystal morphology of the salt (see EP1545733B9) and moltenizing salt crystals while suspended in hot air (see JP09086923A2). Other wet chemical methods are described in U.S. Pat. Pub. No. 2009/0176096 A1 and U.S. Pat. No. 7,220,435.

These and similar reported processes all require many steps and specialized equipment and may be difficult to scale up to large volumes. In addition, these types of processes can have low yields, and frequently use ingredients that reduce the purity of the resulting salt.

SUMMARY

Some embodiments provided herein relate to producing rounded spherical salt particles by moving or agitating the particles in contact with a finishing media. Spherical particles produced in accordance with the present disclosure have a high degree of sphericity and are free from contaminants and impurities associated with other methods. Moreover, the methods of the present disclosure have high yields and do not require expensive or sophisticated machinery to produce.

In some embodiments, a method is provided for producing rounded salt particles from angular salt particles. The method can comprise combining the angular salt particles with a quantity of finishing media in a receptacle. Further, the method can comprise moving or agitating the angular salt particles and the finishing media until the angular salt particles have a sphericity.

In some embodiments, a method is provided for producing rounded salt particles from angular salt particles. The method can comprise providing a quantity of angular salt particles; providing a quantity of finishing media. Further, the method can comprise moving the angular salt particles and the finishing media against each other to cause contact therebetween until the angular salt particles become rounded to a predetermined sphericity.

In some embodiments, a process for manufacturing a soft prosthetic breast implant is provided. The process can comprise adhering on an exterior of a flexible shell of the implant an even distribution of rounded salt particles. The shell can then be cured with the rounded salt particles adhered thereto. Later, the rounded salt particles can be removed by forming an open-pored structure on the exterior of the flexible shell such that the exterior of the flexible shell exhibits an undulating topography. The open-pored structure can comprise round cavities defined by impressions of the rounded salt particles. However, the open-pored structure does not extend through an entire thickness of the silicone elastomer.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

Various features of illustrative embodiments of the present disclosure are described below with reference to the drawings. The illustrated embodiments are intended to illustrate, but not to limit, the present disclosure. The drawings contain the following figures.

DETAILED DESCRIPTION

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding.

The present disclosure relates to the modification of the naturally cubic morphology of common salt crystals, grains or particles, hereinafter referred to generally and interchangeably as "particles."

The present disclosure provides a reliable method to alter substantially cubic or angular salt particles to rounded, spherically or nearly spherically shaped particles. For the sake of simplicity, the salt particles produced by the presently described methods will generally be referred to as "rounded" salt particles, implying a shape that has been modified from the naturally occurring cubic angular-shaped salt.

At least some of the embodiments disclosed herein reflect the realization that ionic crystalline solids naturally form into angular shapes (e.g., cubic, monoclinic, orthorhombic, etc.) because these are the most energetically favorable configurations. Ionic crystalline solids are held together by relatively weak ionic interactions (in contrast to stronger covalent interactions), which are due to the attractions between positively charged cations and negatively charged anions. When an ionic crystalline solid is subjected to a sufficient force, the ionic crystalline solid will naturally break along a crystallographic plane. These types of breaks tend to result in crystals having angular, planar faces.

The tendency of ionic crystalline solids to break across crystallographic planes having angular faces presents a major obstacle to forming spherical salt particles. As an ionic crystalline surface departs from the stable angular form and into a more spherical form, the crystal will incur an increasing amount of strain. On an atomic level, this strain can be due, in part, to charged surface atoms lacking compensating charged species. The result is that ionic crystalline solids like salts can be fragile materials that will break across crystallographic planes rather than form a spherical shape. The presently disclosed methods overcome this problem and result in salt particles having an increased sphericity.

Generally speaking, for purposes of this disclosure, the initial salt particles used in the methods of the present disclosure are sometimes referred to as "angular" or "cubic" particles, whereas the particles produced by the methods of the present disclosure are sometimes referred to as "rounded," "spherical," or "nearly spherical." Also, for purposes of this disclosure, "rounded" particles may include particles that are spherical or nearly spherical. However, "rounded" particles can be defined as having a sphericity greater than a sphericity of the initial angular or cubic particles. Thus, according to some embodiments, a particle becomes "rounded" when, as a result of implementing a method disclosed herein, the sphericity of the particle increases. Further, for purposes of this disclosure, the terms "sphericity," "particle size," or other such measurements of a particle may refer to individual measurements or calculations of a particle or averages of such measurements or calculations of several particles of a sample. For example, sphericity can refer to average sphericity, and particle size can refer to average particle size.

A particle's "sphericity" or "mean circularity" can be determined using the surface area of a sphere having the same volume as the particle, divided by the actual surface area of the particle. For example, a sphericity of 1.00 represents a perfect sphere. In the present disclosure, particle sphericities were determined using a Malvern (Westborough, Mass., USA) Morphologi G3 ID instrument. Other methods for measuring the particle's sphericity may be utilized and will be readily apparent to a person of skill in the art.

In some embodiments, the presently disclosed methods can produce salt particles having a sphericity of greater than 0.750. For example, in some embodiments, the presently disclosed methods can produce salt particles having a sphericity of greater than 0.800, greater than 0.850, greater than 0.900, greater than 0.930, or greater than 0.950. In some embodiments, the presently disclosed methods can produce salt particles having a sphericity of about 0.950, which provides excellent physical properties that are superior to prior alternatives and useful in a variety of industries, such as the textile, dairy, food, fertilizer, paper, pharmaceutical, and medical device industries.

In a broad aspect, the present disclosure produces rounded or nearly spherically shaped salt crystals by abrasion. For example, the method comprises utilizing a mechanical abrading mechanism on existing cubic salt crystals to achieve salt crystals having a desired roundness. Examples of abrading mechanisms include, but are not limited to, shaking, stirring, and vibrating the angular salt particles. In some embodiments, the process utilizes commercially available vibratory finishing equipment to produce rounded salt particles of a predetermined sphericity and at a predetermined size range. In some embodiments, the vibratory finishing equipment is a vibratory bowl.

In some embodiments, the method comprises providing cubic or angular salt crystals and a quantity of a finishing media. Suitable materials to be used for a finishing media include, but are not limited to, ceramics, minerals, metals, alloys, glasses, plastics, polymers, and combinations thereof. Suitable ceramic materials include, but are not limited to, porcelain, aluminum oxide, silicon carbide, and combinations thereof. A non-limiting example of a suitable metal is stainless steel.

The salt crystals and/or the finishing media may be sieved to achieve a desired particle size fraction. The method further comprises vibrating the salt crystals while the salt crystals are in contact with the finishing media.

In some embodiments, the vibrating is performed for a length of time sufficient to cause the salt crystals to be abraded and take on a desired roundedness or sphericity in shape. In some embodiments, the step of vibrating is performed, for example, for at least about 6 hours, for at least about 8 hours, for at least about 10 hours, for at least about 12 hours, for at least about 18 hours, for at least about 24 hours, for at least about 36 hours, for at least about 3 days, for at least about 6 days, for at least about 10 days, or for at least about 12 days. Depending on the equipment used, the treatment time necessary to achieve a desired result can be decreased, for example, by increasing the frequency of movement, such as the rpm of the vibratory bowl.

The salt particles can comprise, for example, any ionic compound that is naturally crystalline, such as ordinary table salt, i.e. sodium chloride (NaCl). The particles may comprise, alternatively, potassium chloride or calcium carbonate, for example, or combinations thereof. Other non-limiting examples of suitable salts include lithium chloride, magnesium chloride, calcium chloride, ammonium chloride, sodium iodide, potassium iodide, lithium iodide, magnesium iodide, calcium iodide, ammonium iodide, sodium bromide, potassium bromide, lithium bromide, magnesium bromide, calcium bromide, ammonium bromide, sodium carbonate, potassium carbonate, lithium carbonate, magnesium carbonate, ammonium carbonate, sodium bicarbonate, potassium bicarbonate, lithium bicarbonate, ammonium bicarbonate, sodium nitrate, potassium nitrate, lithium nitrate, magnesium nitrate, calcium nitrate, ammonium nitrate, sodium acetate, potassium acetate, lithium acetate, magnesium acetate, calcium acetate, ammonium acetate, sodium phosphate, potassium phosphate, lithium phosphate, magnesium phosphate, calcium phosphate, ammonium phosphate, sodium sulfate, potassium sulfate, lithium sulfate, magnesium sulfate, calcium sulfate, or ammonium sulfate, and combinations thereof. A person of skill in the art will recognize the suitability of the present method for several other salt materials not disclosed herein. For use in the manufacture of medical implants, the salt particles are preferably biocompatible and safe to use in human beings.

Sodium chloride cubic crystals are typically available from many sources, for example, Morton Salt is readily and commercially available in a variety of grain sizes. In some embodiments, the initial, angular salt particles have a grain size or particle size of, for example, 100 µm to about 1200 µm, about 200 µm to about 1000 µm, about 400 µm to about 800 µm, or about 500 µm to about 700 µm. In some embodiments, the initial angular salt particles having a size or diameter of about 100 µm, about 200 µm, about 300 µm, about 400 µm, about 500 µm, about 600 µm, about 700 µm, about 800 µm, about 900 µm, about 1000 µm, or about 1200 µm.

In some embodiments, the finishing media comprises non-salt particles, for example, ceramic or metallic particles, for example, ceramic or metallic spheres. In some embodiments, the finishing media comprises stainless steel balls. In some embodiments, the finishing media comprises porcelain ceramic particles, for example porcelain ceramic spheres.

The finishing media may comprise non-salt particles, for example, ceramic or metallic particles, for example, ceramic or metallic spheres, having a diameter of between about 1.0 mm and about 10 mm, about 2 mm to about 8 mm, or about 4 mm to about 6 mm. In some embodiments, the finishing media may comprise non-salt particles having a diameter of about 2 mm, about 3 mm, about 4 mm, about 5 mm, about 6 mm, about 7 mm, about 8 mm, about 9 mm, or about 10 mm.

The size and amount of the finishing media will generally determine the rate and quality of the rounded salt that is produced by the present methods. For example, larger, rougher, heavier, or higher quantity of finishing media (higher finishing media to salt particle quantity ratio) will tend to abrade the salt faster but could lower yields and reduce sphericity. Lighter, smoother finishing media will act more slowly but result in more rounded smoother salt particles with fewer broken or crushed particles.

In some embodiments, the salt particles and the finishing media particles can have a size ratio (salt:finishing media) of about 0.1 to about 1.0, about 0.1 to about 0.5, or about 0.2 to about 0.4. In some embodiments, the salt to finishing media size ratio is about 0.1, about 0.2, about 0.3, about 0.4, about 0.5, about 0.6, about 0.7, about 0.8, about 0.9, or about 1.0.

In some embodiments, the salt to finishing media weight ratio is about 0.5 to about 1.0, about 0.6 to about 0.9, or about 0.7 to about 0.8. In some embodiments, the salt to finishing media weight ratio is about 0.5, about 0.6, about 0.7, about 0.8, about 0.9, or about 1.0.

The rounded, spherical or nearly spherical salt particles produced by the method may have a size, for example, in the range of about 100 µm to about 1200 µm, about 200 µm to about 1000 µm, about 400 µm to about 800 µm, or about 500 µm to about 700 µm. The method may provide, for example, such salt particles having a size or diameter of about 100 µm, about 200 µm, about 300 µm, about 400 µm, about 500 µm, about 600 µm, about 700 µm, about 800 µm, about 900 µm, about 1000 µm, about 1100 µm, or about 1200 µm, depending on the desired use of the product.

In some embodiments, the methods provide rounded crystals of salt having a sphericity (mean circularity) of greater than 0.750, greater than 0.800, greater than 0.850, greater than 0.900, greater than 0.930, or greater than 0.950. A sphericity of 1.000 represents a perfect sphere. In contrast, a naturally occurring salt particle may have a sphericity of less than about 0.750.

For example, the angular salt particles can be placed into a vibratory bowl of commercially available vibratory finishing equipment. The finishing equipment may be, for example, a VibraHone™ FSV-50, available from VibraFinish Company (Simi Valley, Calif., USA). A person of skill in the art will recognize the suitability of other commercially available vibratory finishing equipment. The finishing media can be added to the angular salt particles either before or during the vibration step.

In a specific embodiment, the initial cubic or angular salt particles have a size of about 400 µm to about 600 µm, for example, about 500 µm mean particle size, and the finishing media can comprise ceramic particles having a size of about 2 mm diameter, at about 0.6 ratio of salt to finishing media by weight. The step of vibrating can be performed for a period of hours to one or more days.

The machine with the salt and finishing media mixture can vibrate, which creates a bulk movement or fluidization of the contents in a repeatable flow pattern. The salt crystals are continuously exposed to contact with the finishing media, which slowly abrades the corners and edges of the salt crystals over time. After the desired roundness is achieved, the process is stopped and the resulting mixture is sieved again to remove the fine salt dust and the much larger finishing media, resulting in a simply produced, uniform batch of rounded salt of the desired size. A suitable sieve size will depend on the desired particle size of the resultant rounded salt particles and on the size of the finishing media that is to be separated. In some embodiments, the resulting mixture can be sieved with a sieve mesh size in the range of about No. 16 to about No. 140 (e.g., a −16 140 mesh), about No. 35 to about No. 40, or any sieve mesh size of No. 18, No. 20, No. 25, No. 30, No. 35, No. 40, No. 45, No. 50, No. 60, No. 70, No. 80, No. 100, No. 120, or No. 140.

The present process is simple and repeatable with high expected yields, as well as scalable, for example more or larger machines may be used to provide similar mechanical action.

Medical Implants

In some embodiments, the methods disclosed herein can provide rounded salt particles useful for texturing medical implants, for example, breast implants. The rounded salt particles can have a size of about 400 µm to about 600 µm, for example, about 500 µm. Methods for applying rounded salt particles in the manufacture of textured medical implants are described in detail in U.S. Pat. No. 8,313,527, the entirety of which is incorporated herein by reference. A person of skill in the art would understand how to apply the rounded salt particles formed from the processes described herein as a sacrificial material in the processes for manufacturing these and other medical implants in which a surface texture or other attribute may be desirable.

For example, in some embodiments, a breast implant having an elastomeric silicone shell can be processed to create a desired surface texture by using rounded particles as a sacrificial material. The rounded particles can be those produced by the present methods.

The processes for forming the breast implant generally comprise the steps of forming a flexible shell, adhering on the exterior of the flexible shell a distribution of rounded particles, curing the flexible shell with the rounded particles adhered thereto, and causing or allowing the rounded particles to be removed from the shell thereby leaving impressions of the particles in the shell to create an open-pored structure on a surface thereof.

In some embodiments, the flexible shell is formed of a silicone elastomer. For instance, the flexible shell may be formed of a plurality of layers of different silicone elastomers, or the flexible shell may be formed of a single homogeneous layer of a silicone elastomer.

In some embodiments, the step of forming the flexible shell may comprise dipping a mandrel into a liquid dispersion of elastomeric material. Alternatively, the step of forming comprises rotational molding.

In some embodiments, the step of adhering comprises dipping the flexible shell into a liquid containing the rounded particles, for example, a liquid dispersion or emulsion of rounded particles, for example, rounded salt crystals. Prior to the step of dipping the flexible shell, the process may also include applying a tack coat layer onto the flexible shell.

In some embodiments, the rounded particles comprise rounded crystals of sodium chloride and the solvent is an aqueous composition, for example, water. In some embodiments, the rounded particles comprise a suitable solid material, which is provided in a rounded particulate form, and which is capable of being adhered to a shell, for example, an uncured elastomer shell, and is capable of being dissolved, for example, using a solvent, thereby leaving open, rounded pores in the shell.

In some embodiments, the rounded particles used in accordance with the invention have a substantially uniform particle size of between about 150 microns and about 1450 microns. More specifically, the particles have a maximum particle size range selected from a group of ranges consisting of (1) a range between about 180 microns and about 425 microns, (2) a range between about 425 microns and about 850 microns, and (3) a range between about 850 microns and about 1450 microns. In some embodiments, about 90% of the particles are in the selected particle size range.

In some embodiments, a soft prosthetic breast implant can be formed by a process comprising the steps of forming a flexible shell of silicone elastomer in the shape of a breast implant, adhering on the exterior of the flexible shell a substantially even distribution of rounded particles, curing the flexible shell with the rounded particles adhered thereto, and exposing the flexible shell to a suitable solvent for a sufficient amount of time to dissolve the rounded particles thereby forming an open-pored structure on the exterior of the flexible shell.

In accordance with some embodiments, an implant formed in accordance with the present process can be far superior to an implant made using conventional angular or non-rounded salt crystals instead of rounded salt crystals. For example, in some embodiments, at least one, at least two, or all three of the physical properties of ultimate break force, ultimate elongation, or ultimate tensile strength of an implant formed in accordance with the present process can be superior to an implant made using substantially the same process and the same materials except for conventional angular or non-rounded salt crystals instead of rounded salt crystals.

The step of forming the flexible shell may comprise dipping a mandrel into a liquid dispersion of a shell material, or rotational molding. In some embodiments, the step of forming the flexible shell comprises forming a shell with an opening and the process further includes attaching a patch to cover the opening. The patch may be an unvulcanized elastomer and is attached prior to the step of curing. Alternatively, the step of forming the flexible shell comprises forming a shell with an opening and the process further includes attaching a valve, for example, a one-way valve to cover the opening. The rounded salt crystals may comprise sodium chloride.

EXAMPLES

The following Example is provided for illustrative purposes only, and is not intended to be limiting of the scope of the present disclosure.

Example 1

Spherical Sodium Chloride Particles

Raw (angular, large size dispersion) sodium chloride salt (common table salt or USP grade, e.g. Morton Sodium Chloride USP Granular) was sieved to the size fraction of interest or slightly larger to account for size reduction using US Sieves 30-40, which is about 420 µm to about 600 µm in particle size. 60 lbs. of the salt were combined with 100 lbs. of 4 mm porcelain ceramic balls (Kramer Industries, Piscataway, N.J., USA) into a VibraHone model FSV-50 (VibraFinish Company, Simi Valley, Calif., USA), which has a bowl capacity of 2 cu. ft. The vibratory equipment was operated for 6 hours to 10 days at a frequency of about 2 to about 4 Hz. When the vibrating step was finished the contents of the vibratory bowl and sieved to remove the finishing media and other impurities (e.g., dust) using a sieve size of 35-40. The rounded salt particles were obtained in a yield of 80-90% by weight of the initial quantity of sodium chloride.

Figure 1:
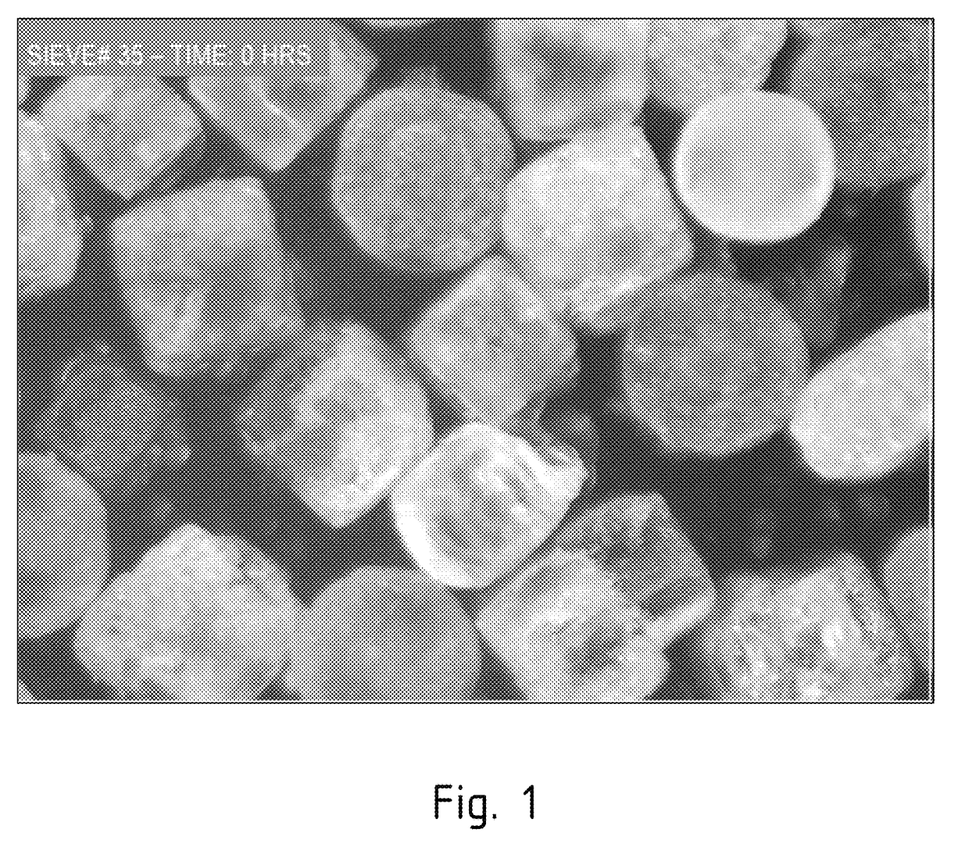
FIG. 1 is a micrograph at 100× magnification of angular sodium chloride particles that have not been processed, in accordance with some embodiments.
Figure 2:
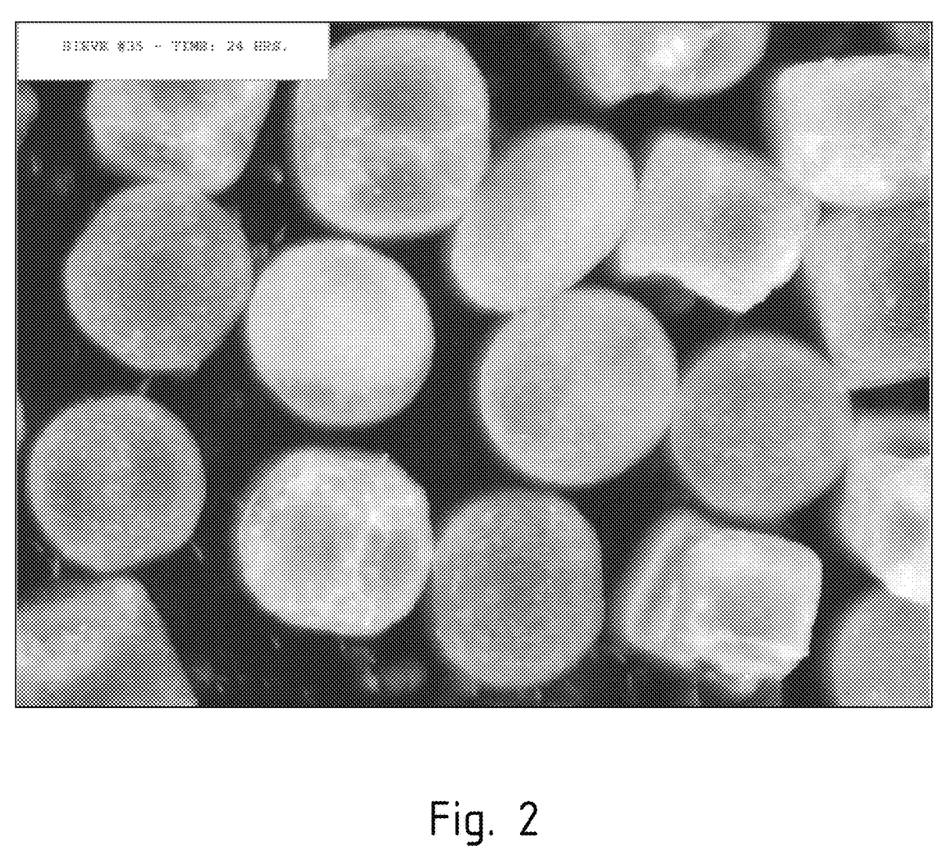
FIG. 2 is a micrograph at 100× magnification of rounded sodium chloride particles after about 24 hours of vibrating, in accordance with some embodiments.
Figure 3:
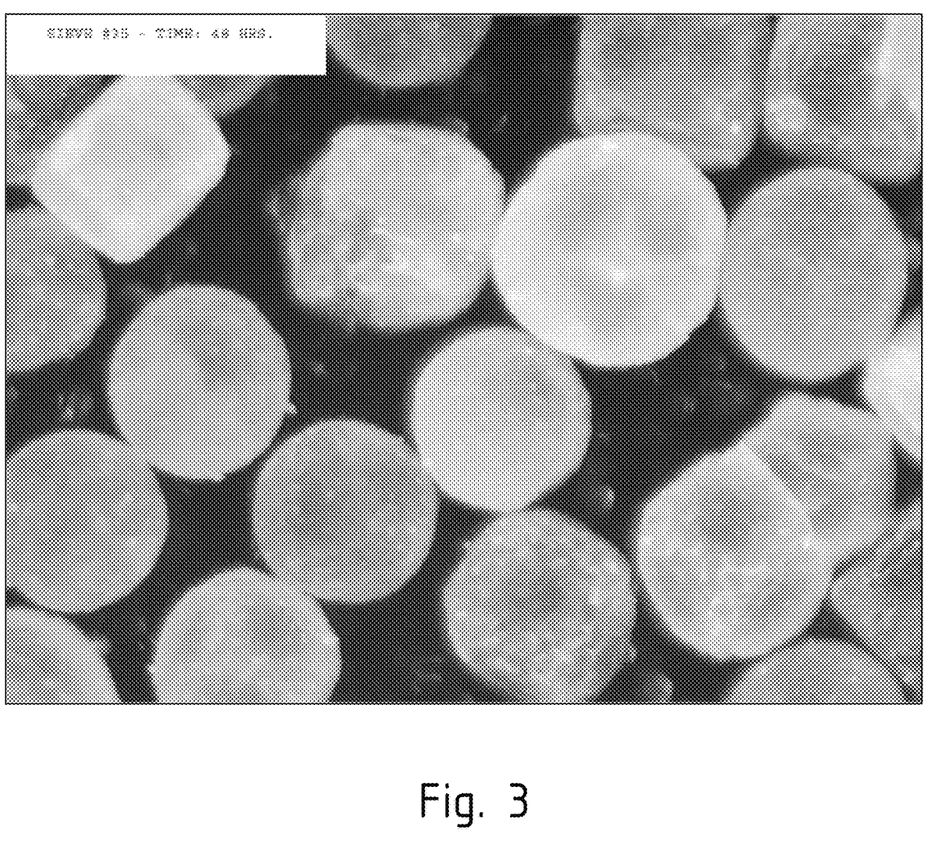
FIG. 3 is a micrograph at 100× magnification of rounded sodium chloride particles after about 48 hours of vibrating, in accordance with some embodiments.
Figure 4:
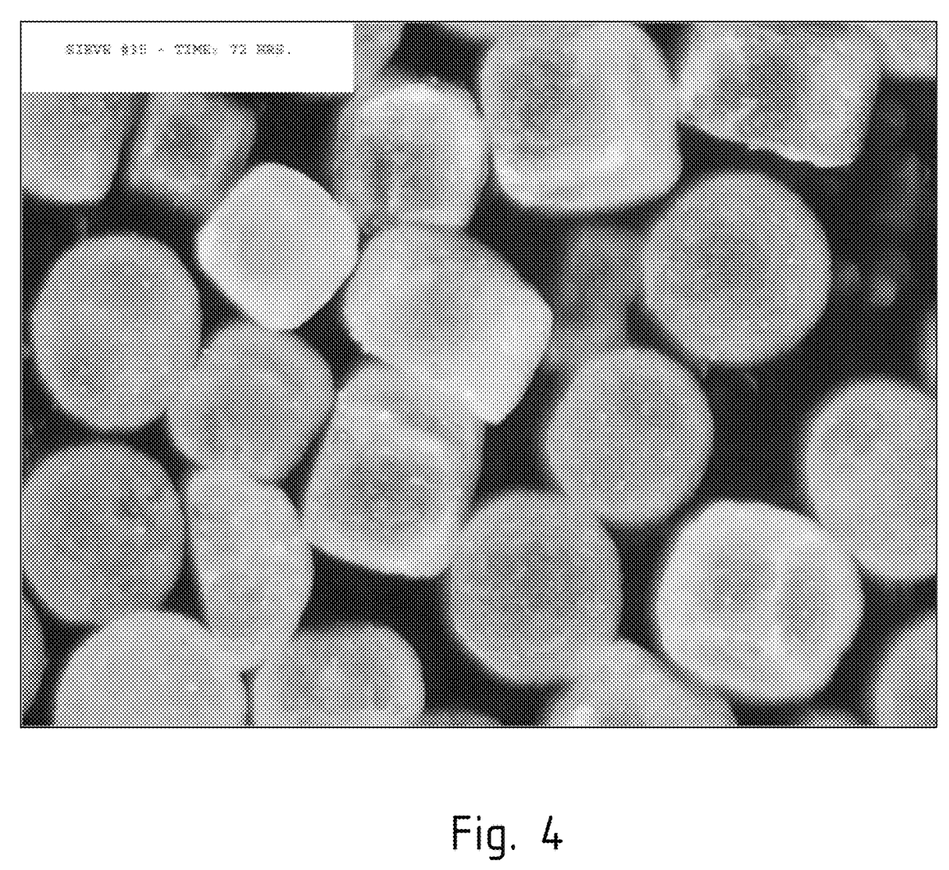
FIG. 4 is a micrograph at 100× magnification of rounded sodium chloride particles after about 72 hours of vibrating, in accordance with some embodiments.
Figure 5:
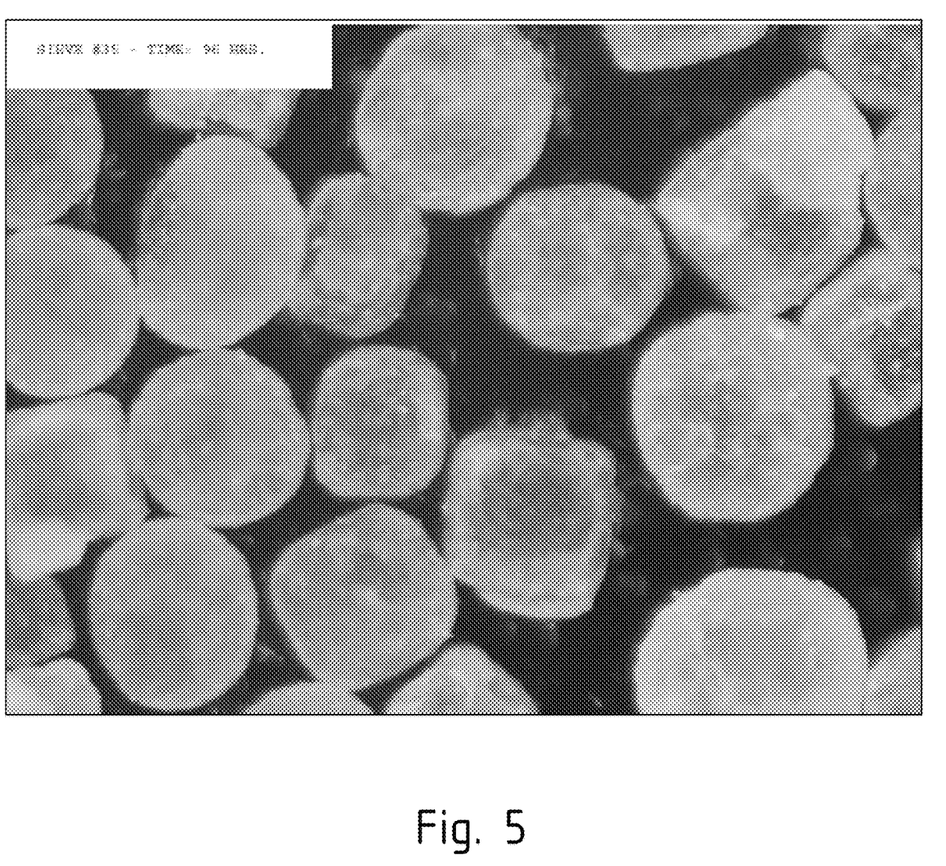
FIG. 5 is a micrograph at 100× magnification of rounded sodium chloride particles after 96 hours of vibrating, in accordance with some embodiments.
Figure 6:
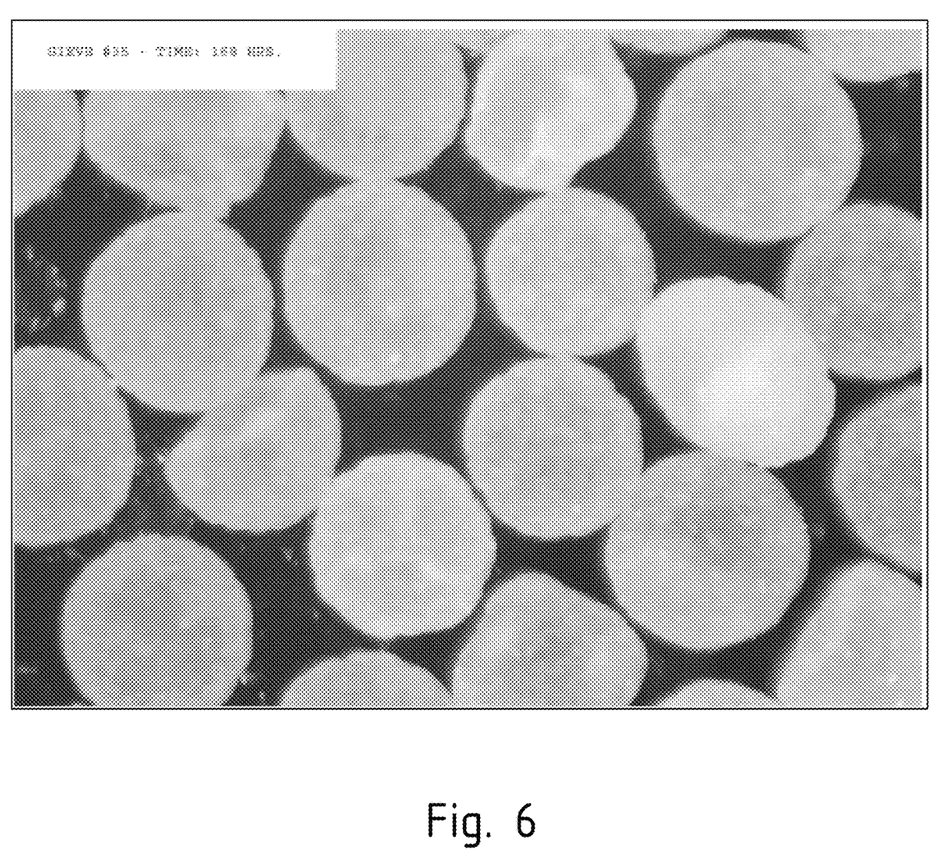
FIG. 6 is a micrograph at 100× magnification of rounded sodium chloride particles after 168 hours of vibrating, in accordance with some embodiments.
Figure 7:
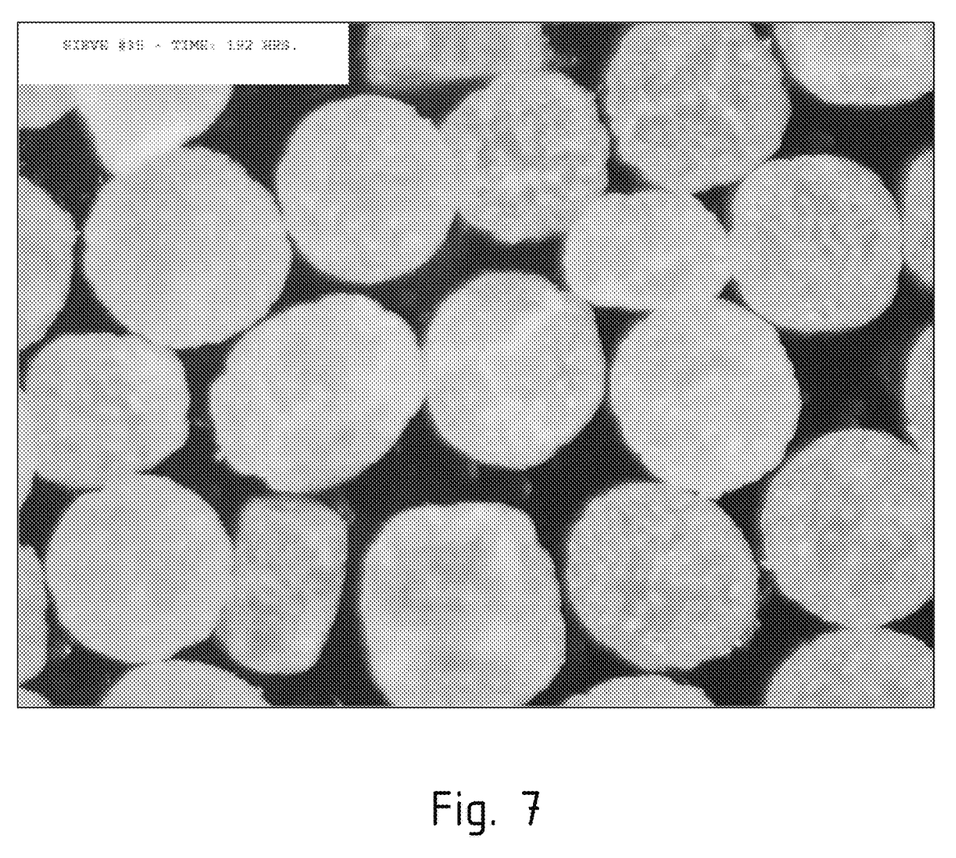
FIG. 7 is a micrograph at 100× magnification of rounded sodium chloride particles after 192 hours of vibrating, in accordance with some embodiments.
Figure 8:
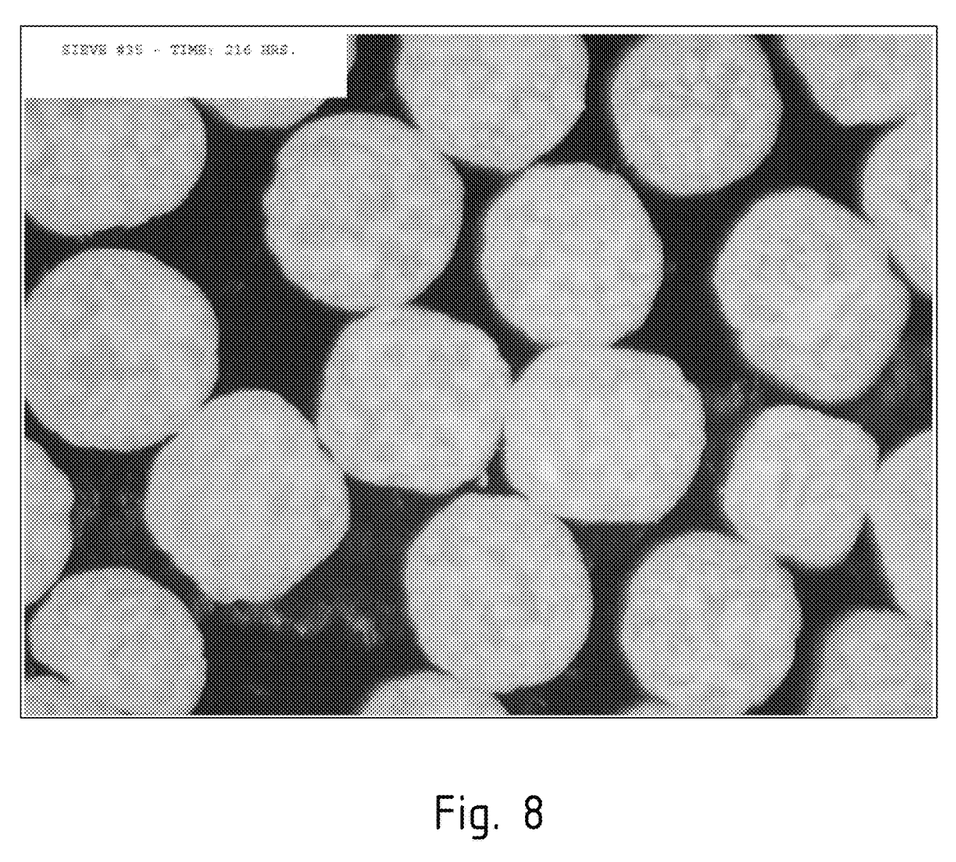
FIG. 8 is a micrograph at 100× magnification of rounded sodium chloride particles after 216 hours of vibrating, in accordance with some embodiments.
Figure 9:
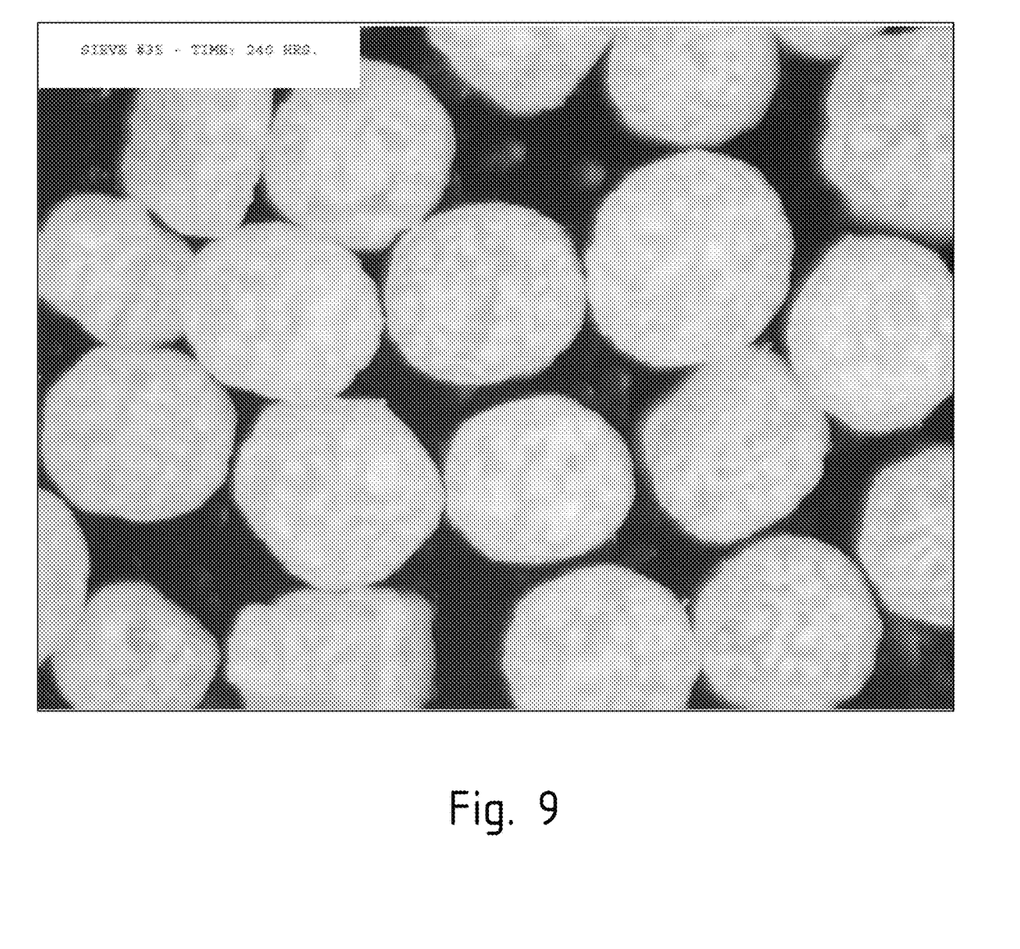
FIG. 9 is a micrograph at 100× magnification of rounded sodium chloride particles after about 240 hours of vibrating, in accordance with some embodiments.

The size and sphericity (mean circularity) of the salt particles product were measured with a Malvern Morphology model G3 ID. The average sphericity of the sodium chloride crystals after processing as described in this Example was greater than 0.900 with several batches reaching an average sphericity of 0.950 or more. In contrast, raw, angular sodium chloride particles had an average sphericity measurement of 0.750 or less. FIG. 1 provides a light microscope micrograph of raw angular sodium chloride particles at 100× magnification. This image shows the angular, cubic nature of the raw particles. FIGS. 2-9 provide light microscope micrographs (100× magnification) of rounded sodium chloride particles after varying times of vibrating. These images show a progressively improving sphericity of the particles with even a period of 24 hours (FIG. 2).

Illustration of Subject Technology as Clauses

Various examples of aspects of the disclosure are described as numbered clauses (1, 2, 3, etc.) for convenience. These are provided as examples, and do not limit the subject technology. Identifications of the figures and reference numbers are provided below merely as examples and for illustrative purposes, and the clauses are not limited by those identifications.

Clause 1. A method for producing rounded salt particles from angular salt particles, the method comprising combining the angular salt particles with a quantity of finishing media in a receptacle, and moving or agitating the angular salt particles and the finishing media until the angular salt particles have a sphericity of greater than about 0.75.

Clause 2. A method for producing rounded salt particles from angular salt particles, the method comprising:
providing a quantity of angular salt particles;
providing a quantity of finishing media; and
moving the angular salt particles and the finishing media against each other to cause contact therebetween until the angular salt particles become rounded to a predetermined sphericity.

Clause 3. The method of any one of the preceding Clauses, further comprising, prior to the moving, sieving angular salt particles to produce the quantity of angular salt particles having a predetermined particle size.

Clause 4. The method of Clause 3, wherein the sieving comprises using a sieve having a sieve mesh size in the range of about No. 16 to about No. 140.

Clause 5. The method of any one of the preceding Clauses, wherein the angular salt particles have a particle size in the range of about 100 to about 1200 µm.

Clause 6. The method of Clause 5, wherein the angular salt particles have a particle size in the range of about 200 to about 1000 µm.

Clause 7. The method of Clause 5, wherein the angular salt particles have a particle size in the range of about 400 to about 800 µm.

Clause 8. The method of Clause 5, wherein the angular salt particles have a particle size of about 400 µm.

Clause 9. The method of Clause 5, wherein the angular salt particles have a particle size of about 500 µm.

Clause 10. The method of Clause 5, wherein the angular salt particles have a particle size of about 600 µm.

Clause 11. The method of any one of the preceding Clauses, wherein the angular salt particles have a sphericity of less than 0.750.

Clause 12. The method of any one of the preceding Clauses, wherein the angular salt particles are selected from the group consisting of sodium chloride, potassium chloride, lithium chloride, magnesium chloride, calcium chloride, ammonium chloride, sodium iodide, potassium iodide, lithium iodide, magnesium iodide, calcium iodide, ammonium iodide, sodium bromide, potassium bromide, lithium bromide, magnesium bromide, calcium bromide, ammonium bromide, sodium carbonate, potassium carbonate, lithium carbonate, magnesium carbonate, ammonium carbonate, sodium bicarbonate, potassium bicarbonate, lithium bicarbonate, ammonium bicarbonate, sodium nitrate, potassium nitrate, lithium nitrate, magnesium nitrate, calcium nitrate, ammonium nitrate, sodium acetate, potassium acetate, lithium acetate, magnesium acetate, calcium acetate, ammonium acetate, sodium phosphate, potassium phosphate, lithium phosphate, magnesium phosphate, calcium phosphate, ammonium phosphate, sodium sulfate, potassium sulfate, lithium sulfate, magnesium sulfate, calcium sulfate, ammonium sulfate, and combinations thereof.

Clause 13. The method of Clause 12, wherein the angular salt particles are selected from sodium chloride, potassium chloride, calcium carbonate, or combinations thereof.

Clause 14. The method of Clause 12, wherein the angular salt particles comprise sodium chloride salt particles.

Clause 15. The method of any one of the preceding Clauses, wherein the finishing media is a material selected from the group consisting of a ceramic, a mineral, a metal, an alloy, a glass, a plastic, and a polymer.

Clause 16. The method of Clause 15, wherein the finishing media comprises a ceramic.

Clause 17. The method of Clause 16, wherein the ceramic is selected from the group consisting of porcelain, aluminum oxide, and silicon carbide.

Clause 18. The method of Clause 16, wherein the ceramic is porcelain.

Clause 19. The method of Clause 15, wherein the finishing media comprises a metal.

Clause 20. The method of Clause 19, wherein the metal is stainless steel.

Clause 21. The method of any one of the preceding Clauses, wherein the finishing media is in a particulate form having a particle size in the range of about 1 mm to about 10 mm.

Clause 22. The method of Clause 21, wherein the particle size is in the range of about 2 mm to about 8 mm.

Clause 23. The method of Clause 21, wherein the particle size is in the range of about 4 mm to about 6 mm.

Clause 24. The method of Clause 21, wherein the particle size is about 1 mm, about 2 mm, about 3 mm, about 4 mm, about 5 mm, about 6 mm, about 7 mm, about 8 mm, about 9 mm, or about 10 mm.

Clause 25. The method of Clause 24, wherein the particle size is about 2 mm.

Clause 26. The method of Clause 24, wherein the particle size is about 4 mm.

Clause 27. The method of any one of the preceding Clauses, wherein the angular salt particles and the finishing media are provided in a weight ratio of angular salt to finishing media in the range of about 0.5:1 to about 1:1.

Clause 28. The method of Clause 27, wherein the angular salt particles and the finishing media are provided in a weight ratio of angular salt to finishing media of about 0.6:1.

Clause 29. The method of Clause 27, wherein the angular salt particles and the finishing media are provided in a weight ratio of angular salt to finishing media of about 1:1.

Clause 30. The method of any one of the preceding Clauses, wherein the moving comprises abrading the angular salt particles with the finishing media.

Clause 31. The method of any one of Clauses 1 to 29, wherein the moving comprises combining the angular salt particles and the finishing media into a mixture and continuously or semi-continuously shaking, vibrating, or stirring the mixture.

Clause 32. The method of Clause 31, wherein the moving comprises vibrating the mixture of angular salt particles and finishing media.

Clause 33. The method of Clause 32, wherein the vibrating is performed using vibratory finishing equipment.

Clause 34. The method of Clause 32, wherein the vibrating is performed using a vibratory bowl.

Clause 35. The method of any one of the preceding Clauses, wherein the moving is performed for a period of time in the range of about 6 hours to about 12 days.

Clause 36. The method of any one of the preceding Clauses, wherein the moving is performed for a period of time in the range of about 7 days to about 10 days.

Clause 37. The method of any one of the preceding Clauses, wherein the moving is performed for at least about 6 hours, about 8 hours, about 12 hours, about 24 hours, about 36 hours, about 3 days, about 6 days, about 10 days, or about 12 days.

Clause 38. The method of Clause 37, wherein the moving is performed for at least about 3 days.

Clause 39. The method of Clause 37, wherein the moving is performed for at least about 6 days.

Clause 40. The method of Clause 37, wherein the moving is performed for at least about 10 days.

Clause 41. The method of any one of Clause 32 to Clause 40, wherein the moving is performed in a cyclical manner at a frequency of about 2 Hz to about 4 Hz.

Clause 42. The method of Clause 41, wherein the moving is performed at a frequency of about 2 Hz.

Clause 43. The method of Clause 41, wherein the moving is performed at a frequency of about 3 Hz.

Clause 44. The method of Clause 41, wherein the moving is performed at a frequency of about 4 Hz.

Clause 45. The method of any one of the preceding Clauses, wherein the predetermined sphericity is greater than about 0.750.

Clause 46. The method of any one of Clause 1 to Clause 44, wherein the predetermined sphericity is greater than about 0.800.

Clause 47. The method of any one of Clause 1 to Clause 44, wherein the predetermined sphericity is greater than about 0.850.

Clause 48. The method of any one of Clause 1 to Clause 44, wherein the predetermined sphericity is greater than about 0.900.

Clause 49. The method of any one of Clause 1 to Clause 44, wherein the predetermined sphericity is between about 0.900 and about 0.950.

Clause 50. The method of any one of Clause 1 to Clause 44, wherein the predetermined sphericity is greater than about 0.950.

Clause 51. The method of any one of the preceding Clauses, further comprising the step of separating the rounded salt particles from the finishing media.

Clause 52. The method of Clause 51, wherein the separating is conducted using a sieve having a sieve mesh size of about No. 16 to about No. 140.

Clause 53. A rounded particle produced by the method of any one of the preceding Clauses.

Clause 54. A process for manufacturing a soft prosthetic breast implant, the process comprising: forming a flexible shell of silicone elastomer, the silicone elastomer having a thickness; adhering on an exterior of the flexible shell an even distribution of the rounded salt particles of Clause 53; curing the flexible shell with the rounded salt particles adhered thereto; removing the rounded salt particles thereby forming an open-pored structure on the exterior of the flexible shell such that the exterior of the flexible shell exhibits an undulating topography, the open-pored structure comprising round cavities defined by impressions of the rounded salt particles; and processing the flexible shell such that it forms a closed envelope; wherein the open-pored structure does not extend through an entire thickness of the silicone elastomer.

Further Considerations

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

In one or more aspects, the terms "about," "substantially," and "approximately" may provide an industry-accepted tolerance for their corresponding terms and/or relativity between items, such as from less than one percent to 5 percent.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

What is claimed is:

1. A method for producing rounded salt particles from angular salt particles, the method comprising combining the angular salt particles with a quantity of about 1 mm to about 10 mm ball-shaped finishing media in a receptacle, and moving or agitating the angular salt particles and the finishing media at a frequency of about 2 Hz to about 4 Hz for about 6 hours to about 12 days until the angular salt particles have a sphericity of greater than about 0.75.

2. The method of claim 1, wherein the angular salt particles have a particle size in the range of about 100 to about 1200 µm.

3. The method of claim 1, wherein the angular salt particles are sodium chloride.

4. The method of claim 1, wherein the finishing media is selected from the group consisting of porcelain, aluminum oxide, and silicon carbide.

5. The method of claim 1, wherein the finishing media is in a particulate form having a particle size of about 4 mm.

6. The method of claim 1, wherein the angular salt particles and the finishing media are provided in a weight ratio of angular salt to finishing media of about 0.6:1.

7. The method of claim 1, wherein the moving comprises combining the angular salt particles and the finishing media into a mixture and continuously or semi-continuously shaking, vibrating, or stirring the mixture.

8. The method of claim 7, wherein the moving comprises vibrating the mixture of angular salt particles and finishing media.

9. The method of claim 1, wherein the moving is performed in a cyclical manner at a frequency of about 2 Hz to about 4 Hz.

10. The method of claim 1, wherein the predetermined sphericity is greater than about 0.900.

11. The method of claim 1, further comprising the step of separating the rounded salt particles from the finishing media.

12. The method of claim 1, wherein the angular salt particles have a particle size in the range of about 420 to about 600 µm.

13. A process for manufacturing a soft prosthetic breast implant, the process comprising:
    forming a flexible shell of silicone elastomer, the silicone elastomer having a thickness;
    adhering on an exterior of the flexible shell an even distribution of the rounded salt particles formed by the method of claim 1;
    curing the flexible shell with the rounded salt particles adhered thereto; and
    removing the rounded salt particles from the exterior of the flexible shell.

14. The process of claim 13, wherein the removing forms an open-pored structure on the exterior of the flexible shell such that the exterior of the flexible shell exhibits an undulating topography, the open-pored structure comprising round cavities defined by impressions of the rounded salt particles.

15. The process of claim 14, wherein the open-pored structure does not extend through an entire thickness of the silicone elastomer.

16. The process of claim 13, further comprising processing the flexible shell such that it forms a closed envelope.

17. A method for producing rounded sodium chloride salt particles from angular sodium chloride salt particles having a particle size in the range of about 420 to about 600 μm, the method comprising:
- combining the angular sodium chloride salt particles with a quantity of 4 mm porcelain ceramic balls in a receptacle, wherein the angular sodium chloride salt particles and the porcelain ceramic balls are provided in a weight ratio of angular salt to finishing media is about 0.6:1; and
- vibrating the angular sodium chloride salt particles and the porcelain ceramic balls until the angular sodium chloride salt particles have a sphericity of greater than about 0.75, wherein the vibrating is performed for a period of time in the range of about 6 hours to about 12 days and at a frequency of about 2 Hz to about 4 Hz.

18. The method of claim 17, wherein the vibrating the angular sodium chloride salt particles and the porcelain ceramic balls comprises continuously vibrating the angular sodium chloride salt particles and the porcelain ceramic balls.

19. The method of claim 17, wherein the vibrating the angular sodium chloride salt particles and the porcelain ceramic balls comprises semi-continuously vibrating the angular sodium chloride salt particles and the porcelain ceramic balls.

20. The method of claim 17, wherein the predetermined sphericity is greater than about 0.900.

21. The method of claim 17, further comprising the step of separating the rounded sodium chloride salt particles from the porcelain ceramic balls.

\* \* \* \* \*